United States Patent
Wuenn et al.

(10) Patent No.: US 8,779,388 B2
(45) Date of Patent: Jul. 15, 2014

(54) OPTICAL SENSOR AND DEVICE THEREWITH, AND METHOD FOR THE PRODUCTION THEREOF

(75) Inventors: Eberhard Wuenn, Goettingen (DE); Reinhard Baumfalk, Goettingen (DE); Daniel Riechers, Hannover (DE); Julia Lueders, Lahstedt (DE)

(73) Assignee: Sartorius Stedim Biotech GmbH (DE)

( * ) Notice: Subject to any disclaimer, the term of this patent is extended or adjusted under 35 U.S.C. 154(b) by 52 days.

(21) Appl. No.: 13/143,509

(22) PCT Filed: Dec. 3, 2009

(86) PCT No.: PCT/EP2009/008604
§ 371 (c)(1),
(2), (4) Date: Jul. 6, 2011

(87) PCT Pub. No.: WO2010/078893
PCT Pub. Date: Jul. 15, 2010

(65) Prior Publication Data
US 2011/0266449 A1  Nov. 3, 2011

(30) Foreign Application Priority Data
Jan. 7, 2009  (DE) .................. 10 2009 003 971

(51) Int. Cl.
*F21V 9/16* (2006.01)
*G01N 21/80* (2006.01)

(52) U.S. Cl.
CPC ...................................... *G01N 21/80* (2013.01)
USPC ...................... 250/458.1; 359/350; 250/361 R

(58) Field of Classification Search
CPC .................................................... G01N 21/80
USPC ................... 250/458.1, 361 R, 492.1, 492.2, 250/492.21–492.24; 422/563; 359/350
See application file for complete search history.

(56) References Cited

U.S. PATENT DOCUMENTS

| | | | |
|---|---|---|---|
| 5,091,800 A * | 2/1992 | Offenbacher et al. | 359/350 |
| 5,968,326 A * | 10/1999 | Yelon et al. | 204/296 |
| 6,207,110 B1 * | 3/2001 | Sullivan et al. | 422/429 |
| 6,288,420 B1 * | 9/2001 | Zhang et al. | 257/295 |
| 6,951,715 B2 * | 10/2005 | Cunningham et al. | 435/4 |
| 7,390,462 B2 | 6/2008 | Rao et al. | |
| 2005/0249667 A1 * | 11/2005 | Tuszynski et al. | 424/9.3 |
| 2006/0257996 A1 * | 11/2006 | Simpson et al. | 435/287.2 |

FOREIGN PATENT DOCUMENTS

| | | |
|---|---|---|
| DE | 100 51 220 | 4/2002 |
| EP | 0 300 990 | 1/1989 |
| EP | 0 584 721 | 3/1994 |
| WO | 00/11471 | 3/2000 |
| WO | 02/056023 | 7/2002 |
| WO | 2004/077035 | 9/2004 |

* cited by examiner

*Primary Examiner* — David Porta
*Assistant Examiner* — Taeho Jo
(74) *Attorney, Agent, or Firm* — Gerald E. Hespos; Michael J. Porco; Matthew T. Hespos

(57) ABSTRACT

An optical sensor is provided with reduced sensitivity toward external light influences, fluorophores, and radiation, more particularly gamma radiation. The sensor is suitable for determining at least one parameter in a medium. The sensor has a matrix that contains a fluorescent dye. The matrix is supported by a transparent substrate and has a precious metal layer on the side facing the medium. The precious metal layer provides protection against photobleaching and radiation. The optical sensor is suitable for implementation in containers and laboratory products that are sterilized by gamma radiation, such as disposable bioreactors.

30 Claims, 1 Drawing Sheet

OPTICAL SENSOR AND DEVICE THEREWITH, AND METHOD FOR THE PRODUCTION THEREOF

BACKGROUND OF THE INVENTION

1. Field of the Invention

The invention relates to an optical sensor, which can be sterilized by irradiation, for determining at least one parameter in a medium, to a device with such an optical sensor, and to a method for producing the sensor and the device.

2. Description of the Related Art

Optical sensors are used, in particular, in disposable, mixing and bioreactors or containers in medical technology and biotechnology. In these and similar fields of application, it is often necessary to sterilize a container before use. In the field of disposable products, sterilization by radiation, more particularly gamma radiation, has proven its worth; however, this can be damaging to the optical sensors. Hence such sensors require an effective protective system that can simultaneously be implemented in a cost-effective fashion.

WO 02/056023 A1 and DE 10,051,220 A1 have disclosed optical sensors for measuring at least one parameter in a sample. These sensors are based on a device for exciting fluorescence in an analyte-sensitive fluorescent dye, which is immobilized in a sample vessel or reactor in a matrix and is in at least indirect contact with the sample, and an evaluation device for the resulting fluorescent response signal. The analyte concentration can be evaluated or determined here by using both the fluorescence decay time and the fluorescence intensity. A disadvantageous intrinsic problem of these sensor systems emerges from the photobleaching of the utilized fluorescent dyes, which is detrimental to the long-term performance of these sensors as a result of a gradual reduction in the signal-to-noise ratio. Photobleaching is caused both by the actual measurement and the associated excitation of the fluorophore by light with a suitable wavelength and by external light, which can for example pass through the wall of a transparent bioreactor from the outside. Furthermore, the measurement can be falsified by interaction between the fluorescence excitation light and the fluorophores present in the sample.

U.S. Pat. No. 7,390,462 B2 has disclosed a sensor in which the fluorescent dye is present in an immobilized fashion in a hydrophilic matrix. Said document claims a sensor with the pH-sensitive fluorescent dye MA-HPDS, present in a hydrogel. A disadvantage therein is that such hydrophilic optical sensors are damaged in a dose-dependent fashion during sterilization with gamma radiation. Such radiation is particularly applied in laboratory technology in the case of containers made of polymers. Both the intensity of the fluorescence of the dye or dyes and the sensitivity of the sensor with respect to the measurement variable are reduced. Such a sensor is particularly damaged if, during the gamma sterilization, it is in contact with a relatively large volume of air or other conventional shielding gasses as well, such as nitrogen or argon. The gasses are partly ionized during the gamma sterilization. These ions and radical ions react with the walls during the sterilization of a gas-filled polymer container, but also with the dyes located in the sensors. Sensors based on porous, hydrophilic matrices are particularly susceptible to this because, as a result of the principles, the sensor chemicals have to present in immobilized fashion on the surface or inner surface of the matrix so that the sample to be measured can come into contact with the sensor chemicals. The extent of the damage firstly depends on the radiation dose and secondly depends on the surface-to-volume ratio of the irradiated container that contains the sensor. This ratio determines the number of ions and radical ions that damage the sensor or the sensor chemicals contained therein.

The invention is therefore based on the object of firstly developing an optical sensor and a device therewith, the sensitivity of which is reduced with respect to influences of external light, fluorophores, and radiation, more particularly gamma radiation, and secondly developing a method for the production thereof.

SUMMARY OF THE INVENTION

The optical sensor according to the invention measures one or more parameters in a medium. The sensor substantially has three layers layered one above the other. A transparent substrate serves as a base layer. Thereupon there is a matrix that contains at least one fluorescent dye. In order to protect the last-mentioned layer, a precious metal layer is applied thereon. This precious metal layer ensures optical insulation from external-light influences and fluorophores. The fluorescent light from fluorophores, such as e.g. NADPH or riboflavin, in a culture broth surrounding the sensor is insulated by the precious metal layer, as a result of which a disadvantageous influence of the fluorophores in the culture broth on the measurement is prevented. Additionally, the sensitivity with respect to reactive particles created during gamma irradiation is greatly reduced. This also achieves a better signal-to-noise ratio and a generally increased sensitivity of the sensor element with respect to its measurement variable. At the same time, precious metals are inert with respect to aqueous solutions and cell-culture or fermentation media conventional in biotechnology or pharmaceutics. The precious metal layer additionally fulfills a securing and stabilizing function with respect to the sensor chemicals situated therebelow in the form of the matrix containing the at least one fluorescent dye.

As per a preferred embodiment of the invention, the optical sensor can be sterilized by radiation and maintain its functionality in the process. The sensitivity with respect to sterilization, for example by means of ionizing radiation, gamma radiation, UV-C, beta, or electron radiation is greatly reduced as a result of the precious metal layer. The reactive ions and radicals formed in the gas phase surrounding the sensor by the radiation no longer react with the matrix and the fluorescent dye or fluorescent dyes themselves. Hence, this achieves a better signal-to-noise ratio and a generally higher sensitivity of the optical sensor with respect to its measurement variable. Herein, the measurement variables can be e.g. the pH-value, the dissolved oxygen concentration or other parameters.

As per a further preferred embodiment of the invention, the matrix of the optical sensor is hydrophilic. Special embodiments can be a sol-gel matrix or a hydrogel, in which the fluorescent dye is present in an immobilized fashion. The hydrophilic property is particularly required for optical sensors whose fluorescent dye, which is embedded in the matrix, must be accessible to an aqueous medium. It is in the nature of optical sensors with a hydrophilic matrix to be very sensitive to sterilization, for example by means of gamma radiation. The precious metal layer effectively protects against these influences.

As per a particularly preferred embodiment of the invention, the matrix of the optical sensor is porous and the precious metal layer does not close-off this porous matrix because contact must often still be possible between the sensor chemicals and the medium to be measured. Optical sensors that require this hence can contact the medium directly. This is achieved by the peak-to-valley height of the surface substantially having a larger value than the layer thickness of the precious metal layer. A porous matrix with an uneven surface additionally is advantageous in that the precious metal layer is applied in a simple and cost-effective fashion because such a surface provides the precious metal layer to be applied thereon with a corresponding structure that does not close-off the porous matrix. The precious metal layer itself does not have to be perforated again or applied in places in a corresponding fashion. Moreover, applying the precious metal layers refines the openings on the surface from a cross-sectional standpoint, which allows a cost-effective production method of the matrix.

In a further preferred embodiment of the invention, the precious metal layer of the optical sensor is applied by vapor deposition. In this context, it was found to be particularly advantageous to have a layer thickness of between 20 and 200 nm because this ensures optical insulation with respect to external light.

According to a particularly preferred embodiment of the invention, the precious metal layer is made of gold, platinum, palladium or a combination thereof. These materials are inert with respect to aqueous solutions or cell-culture or fermentation media conventional in biotechnology or pharmaceutics. At the same time, precious metals are durable materials and can additionally provide the matrix with stability and robustness.

In a further preferred embodiment of the invention. A device for holding a medium has at least one optical sensor according to the invention, which measures one or more parameters in the medium. The sensor substantially contains three layers layered one above the other. A transparent substrate serves as a base layer. Thereupon there is a matrix that contains at least one fluorescent dye. In order to protect the last-mentioned layer, a precious metal layer is applied thereon. This precious metal layer ensures optical insulation from external-light influences and fluorophores. The fluorescent light from fluorophores, such as e.g. NADPH or riboflavin, in a culture broth surrounding the sensor is insulated by the precious metal layer and an influence of the fluorophores on the measurement is prevented or greatly reduced. Additionally, the sensitivity with respect to gamma radiation is greatly reduced. This also achieves a better signal-to-noise ratio and a generally increased sensitivity of the sensor element with respect to its measurement variable. At the same time, precious metals are inert with respect to aqueous solutions and cell-culture or fermentation media conventional in biotechnology or pharmaceutics. The precious metal layer additionally fulfills securing and stabilizing functions with respect to the sensor chemicals situated therebelow in the form of the matrix containing the at least one fluorescent dye.

As per a preferred embodiment of the invention, the device can be sterilized by radiation and maintain its functionality in the process. The sensitivity with respect to sterilization, for example by means of ionizing radiation, gamma radiation, ionizing radiation, gamma radiation, UV-C, beta, or electron radiation is greatly reduced as a result of the precious metal layer. The reactive ions and radicals formed in the gas phase surrounding the sensor by the radiation no longer react with the matrix or the immobilized fluorescent dye itself. Hence, this achieves a better signal-to-noise ratio and a generally higher sensitivity of the optical sensor with respect to its measurement variable. Herein, the measurement variables can be e.g. the pH-value, the oxygen value or other parameters.

As per a further preferred embodiment of the invention, the matrix of the optical sensor of the device is hydrophilic. Special embodiments can be a sol-gel matrix or a hydrogel, in which the fluorescent dye is present in an immobilized fashion. The hydrophilic property is particularly required for optical sensors whose fluorescent dye, which is embedded in the matrix, must be accessible to an aqueous medium. It is in the nature of optical sensors with a hydrophilic matrix to be very sensitive to sterilization, for example by means of gamma radiation. The precious metal layer effectively protects against these influences.

As per a particularly preferred embodiment of the invention, the matrix of the optical sensor is porous and the precious metal layer does not close-off this porous matrix because contact must often still be possible between the sensor chemicals and the medium to be measured. Optical sensors that require this hence can contact the medium directly. This is achieved by the peak-to-valley height of the surface substantially having a larger value than the layer thickness of the precious metal layer. A porous matrix with an uneven surface additionally is advantageous in that the precious metal layer is applied in a simple and cost-effective fashion because such a surface provides the precious metal layer to be applied thereon with a corresponding structure that does not close-off the porous matrix. The precious metal layer itself does not have to be perforated again or applied in places in a corresponding fashion. Moreover, applying the precious metal layers refines the openings on the surface from a cross-sectional standpoint, which allows a cost-effective production method of the matrix.

In a further preferred embodiment of the invention, the precious metal layer of the optical sensor is applied by vapor deposition. In this context, it was found to be particularly advantageous to have a layer thickness of between 20 and 200 nm because this ensures optical insulation with respect to external light.

According to a particularly preferred embodiment of the invention, the precious metal layer is made of gold, platinum, palladium or a combination thereof. These materials are inert with respect to aqueous solutions or cell-culture or fermentation media conventional in biotechnology or pharmaceutics. At the same time, precious metals are durable materials and can additionally provide the matrix with stability and robustness.

According to another preferred embodiment of the invention, the device has a transmitter and/or receiver for wireless communication. Hence measurement results can be transmitted without a cable, and instructions such as the measurement frequency for example can also be given to the optical sensor or the device without wires. Examples for this are RFID or Bluetooth technology.

In a preferred method as per the invention, substantially two steps are applied during the production of an optical sensor. Firstly, the step of applying a matrix with at least one fluorescent dye onto a transparent substrate and secondly the step of applying a precious metal layer onto the matrix. The precious metal layer ensures optical insulation from external-light influences and fluorophores. The fluorescent light from fluorophores, such as e.g. NADPH or riboflavin, in a culture broth surrounding the sensor is insulated by the precious metal layer and an influence of the fluorophores on the measurement is prevented or greatly reduced. Additionally, the sensitivity with respect to gamma radiation is greatly reduced. This also achieves a better signal-to-noise ratio and a generally higher sensitivity of the sensor element with respect to its measurement variable. At the same time, precious metals are inert with respect to aqueous solutions and cell-culture or fermentation media conventional in biotechnology or pharmaceutics. The precious metal layer additionally fulfills securing and stabilizing functions with respect to the sensor chemicals situated therebelow in the form of the matrix containing the at least one fluorescent dye.

In a particularly preferred embodiment of the method as per the invention, the precious metal layer is applied to the matrix by vapor deposition. The vapor deposition can be brought about by thermal evaporation. By way of example, different variants of CVD include incandescent-filament, laser or arc evaporation. The precious metal layer can particularly preferably be applied by physical vapor deposition (PVD) or sputtering. PVD for applying the precious metal layer preferably occurs at a pressure of between $10^{-2}$ Pa and 10 Pa, a sputtering voltage of between 800 V and 3000 V and a sputtering current of between 10 mA and 50 mA. Different variants include e.g. direct-current, high-frequency, and magnetron sputtering, or mixed forms thereof. Magnetron sputtering at a pressure of 1 Pa, a sputtering current of 50 mA, and a sputtering time of 5 minutes is particularly preferred. In the case of sputtering, the sample to be coated is barely heated during the process and hence it is spared. This method can be used to apply a corresponding thin layer evenly in a quick, effective, and cost-effective fashion.

In the case of a particularly preferred method according to the invention, substantially two steps are applied for producing a device: the optical sensor is combined with the device for holding the medium. The device is moreover irradiated by radiation. It is also possible to combine a plurality of optical sensors with the device, wherein an optical sensor can determine at least one parameter in a medium. The functionality of the optical sensor remains despite being irradiated. At the same time the optical sensor is protected from influences by external light and the influence of fluorophores on the measurement.

In a preferred method according to the invention, the device is irradiated by ionizing radiation, for example by gamma, UV-C, beta or electron radiation.

In a further particularly preferred method, a container made of plastic with at least partly flexible walls is used for the device. Such containers can be produced in a cost-effective fashion. Moreover, time-consuming and costly cleaning can be dispensed with in the case of disposable products. One or more optical sensors can be implemented in a container made of plastic. The sensor measurement power is maintained despite a necessary sterilization of the plastic container using radiation.

The invention should be explained in more detail using the exemplary embodiment presented below.

DETAILED DESCRIPTION OF THE PREFERRED EMBODIMENTS

Figure 1:
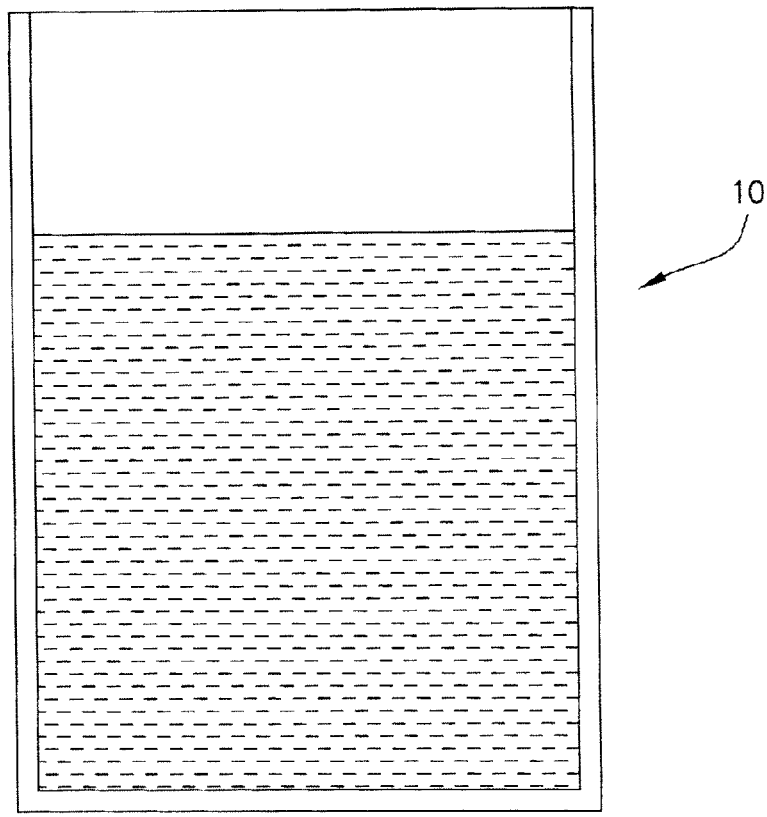
FIG. 1 is a schematic illustration of a container in accordance with the invention.

A container in accordance with the invention is identified by the numeral 10 in FIG. 1. The container 20 preferably is made of plastic with at least partly flexible walls. The container 10 preferably is disposable and preferably is formed from a plastic that can be sterilized by radiation.

Figure 2:
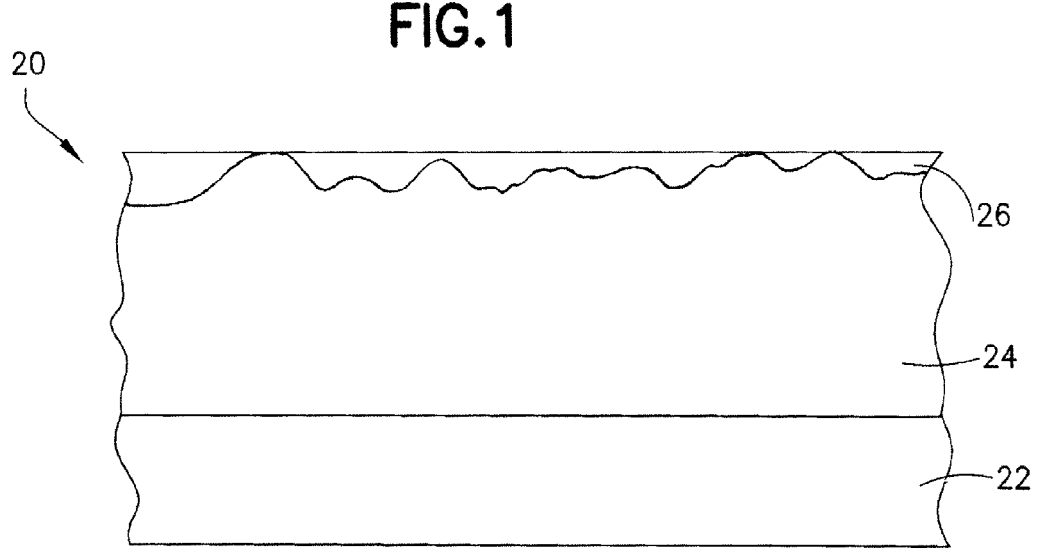
FIG. 2 is a schematic illustration of an optical sensor in accordance with the invention and usable with the container of FIG. 1 or with other containers.

The container 10 is used with an optical sensor identified generally by the numeral 20 in FIG. 2. The sensor 20 comprises three layers one above the other. More particularly, the sensor 20 has a transparent substrate 22 as a base layer. A matrix 24 that contains at least one fluorescent dye is disposed on the transparent substrate 22. A precious metal layer 26 is applied on the matrix 24 to protect the matrix 24 and to ensure optical insulation from external light influences and fluorophores.

Example

Plastic containers 10 (Cultibag RM, Sartorius Stedim Biotech GmbH, Göttingen/Volume: 10 l) are equipped with the optical sensors 20 according to the invention (pH-Sensors Type HP8, Presens GmbH, Regensburg) on a polycarbonate cap. The gold layer 26 is applied by means of magnetron sputtering (EMITECH K550 sputter coater and gold target; parameters: pressure: 1 Pa atmospheric pressure, sputtering current: 50 mA, sputtering time: 5 minutes), with the layer thickness being 150 nm. The sensors 20 are applied centrally in the interior of the container and directly next to sensors of the same type without a gold layer, with the sensor chemicals facing the center of the container. The device 10 is subsequently filled with 10 l of air or nitrogen ($N_2$) and packaged in black, light-opaque PE-bags. Thereupon there is gamma-irradiation at 5.8 kGy and 26.2 kGy (Co-60 source, Beta-Gamma-Service GmbH & Co. KG, Wiehl).

After irradiation, the sensors 20 are removed from the containers and measured by a transmitter (pH-1 mini, Presens GmbH) in buffers with pH-values of 6.0 and 8.0.

The sensitivity (here: the difference in the phases at pH 6.0 and pH 8.0) of the sensors 20 irradiated in nitrogen and in air is comparable. At a dose of 26.2 kGy, the sensors have a very low sensitivity ($\leq 2.80$). The intensity reduces by up to 99% (nitrogen) or 80% (air) from the sensor irradiated at 5.8 kGy to the sensor irradiated at 26.2 kGy.

A sensor not coated with gold has the phase differences between pH 8.0 and pH 6.0 specified in the following table:

| Gas | Gamma ray dose [kGy] | Δ Phase [°] | Amplitude reduction |
|---|---|---|---|
| $N_2$ | 5.8 | 27.1 | 99% |
| $N_2$ | 26.2 | 2.7 | |
| Air | 5.8 | 25.3 | 80% |
| Air | 26.2 | 2.8 | |

By contrast, a sensor 20 coated with gold is still sensitive after 26.2 kGy and has, compared to a gold-coated sensor irradiated at 5.8 kGy, only lost 3% of its intensity, as emerges from the following table:

| Gas | Gamma ray dose [kGy] | Δ Phase [°] | Amplitude reduction |
|---|---|---|---|
| $N_2$ | 5.8 | 29.2 | 3% |
| Air | 26.2 | 23.8 | |

The invention claimed is:

1. An optical sensor for determining at least one parameter in a medium, the sensor comprising at least one matrix that has opposite first and second surfaces and that contains at least one fluorescent dye; a transparent substrate on the first surface of the matrix and supporting the matrix; and a precious metal layer on the second surface of the matrix opposite the transparent substrate and facing the medium, the second surface of the matrix being an uneven surface with peaks and valleys defining a peak-to-valley height larger than a thickness of the precious metal layer so that the precious metal layer does not completely close off the matrix.

2. The optical sensor of claim 1, formed from materials that can be sterilized by radiation and maintain its functionality after the sterilization.

3. The optical sensor of claim 2, wherein the radiation is ionizing radiation.

4. The optical sensor of claim 2, wherein the radiation is gamma radiation.

5. The optical sensor of claim 2, wherein the radiation is electron radiation.

6. The optical sensor of claim 1, wherein the matrix is hydrophilic.

7. The optical sensor of claim 1, wherein the matrix is porous.

8. The optical sensor of claim 1, wherein the matrix is sol-gel matrix or a hydrogel.

9. The optical sensor of claim 1, wherein the precious metal layer is applied by vapor deposition.

10. The optical sensor of claim 1, wherein the precious metal layer has a thickness of between 10 nm and 200 nm.

11. The optical sensor of claim 1, wherein the precious metal layer is made of gold, platinum, palladium or a combination thereof.

12. A device for holding a medium, with an optical sensor for determining at least one parameter in the medium, wherein the optical sensor has at least one matrix that has opposite first and second surfaces and that contains at least one fluorescent dye; a transparent substrate on the first surface of the matrix and supporting the matrix; and a precious metal layer on the second surface of the matrix opposite the transparent substrate and facing the medium, the second surface of the matrix being an uneven surface with peaks and valleys defining a peak-to-valley height larger than a thickness of the precious metal layer so that the precious metal layer does not completely close off the matrix.

13. The device of claim 12, which can be sterilized by radiation and maintain its functionality after the sterilization.

14. The device of claim 13, wherein the radiation is ionizing radiation.

15. The device of claim 13, wherein the radiation is gamma radiation.

16. The device of claim 13, wherein the radiation is electron radiation.

17. The device of claim 12, wherein the matrix is hydrophilic.

18. The device of claim 12, wherein the matrix is porous.

19. The device of claim 12, wherein the matrix is a sol-gel matrix or a hydrogel.

20. The device of claim 12, wherein the precious metal layer is applied by vapor deposition.

21. The device of claim 12, wherein the precious metal layer has a thickness of between 10 nm and 200 nm.

22. The device of claim 12, where in the precious metal layer is made of gold, platinum, palladium or a combination thereof.

23. The device of claim 12, which has a transmitter and/or receiver for wireless communication.

24. A method for producing an optical sensor comprising the steps of:
applying a matrix with at least one fluorescent dye onto a transparent substrate so that a surface of the matrix facing away from the transparent surface is uneven with peaks and valleys defining a peak-to-valley height; and
applying a precious metal layer onto the surface of the matrix facing away from the transparent substrate, the precious metal layer having a thickness less than the peak-to valley height on the surface of the matrix so that the precious metal layer does not completely close off the matrix.

25. The method of claim 24, wherein the precious metal layer is applied onto the matrix by sputtering in a pressure range of between $10^{-5}$ and 10 Pa, a sputtering voltage of between 800 and 3000 V, and a sputtering current of between 10 and 70 mA.

26. A method for producing a device for holding a medium and comprising the steps of:
providing an optical sensor for determining at least one parameter of the medium, the optical sensor having a transparent substrate, at least one matrix that contains a least one fluorescent dye disposed on the transparent substrate, a surface of the matrix facing away from the transparent surface being uneven with peaks and valleys defining a peak-to-valley height and a precious metal layer on the surface of the matrix opposite the substrate, the precious metal layer having a thickness less than the peak-to valley height on the surface of the matrix so that the precious metal layer does not completely close off the matrix;
combining the optical sensor with the device for holding the medium; and
irradiating the device with the radiation, wherein the sensor maintains its functionality after the irradiation.

27. The method of claim 26, wherein the device is irradiated by ionizing radiation.

28. The method of claim 26, wherein the device is irradiated by electron radiation.

29. The method of claim 26, wherein the device is irradiated by gamma radiation.

30. The method of claim 26, wherein a container made of plastic with at least partly flexible walls is used for the device.

* * * * *